United States Patent
Takahashi

[11] Patent Number: 6,071,295
[45] Date of Patent: Jun. 6, 2000

[54] DEVICE TO HOLD AN ANASTOMOTIC SITE OF CORONARY ARTERY MOTIONLESS AND BLOODLESS FOR THE BYPASS OPERATION

[75] Inventor: Masao Takahashi, Kanagawa, Japan

[73] Assignee: Medivas OPCAB, Inc., La Jolla, Calif.

[21] Appl. No.: 09/171,774

[22] PCT Filed: Nov. 20, 1997

[86] PCT No.: PCT/JP97/04230

§ 371 Date: Oct. 26, 1998

§ 102(e) Date: Oct. 26, 1998

[87] PCT Pub. No.: WO98/37814

PCT Pub. Date: Sep. 3, 1998

[30] Foreign Application Priority Data

Feb. 27, 1997 [JP] Japan ..................... 9-044317

[51] Int. Cl.[7] ............................................. A61M 29/00
[52] U.S. Cl. ........................................ 606/191; 604/176
[58] Field of Search ............... 606/191, 1; 128/897–898; 604/95–96, 176

[56] References Cited

U.S. PATENT DOCUMENTS

| | | | |
|---|---|---|---|
| 3,577,982 | 5/1971 | La Par | 128/245 |
| 3,720,433 | 3/1973 | Rosfelder | 294/64 R |
| 3,858,926 | 1/1975 | Ottenhues | 294/64 R |
| 4,047,532 | 9/1977 | Phillips et al. | 128/303 R |
| 4,447,227 | 5/1984 | Kotsanis | 604/95 |
| 4,627,421 | 12/1986 | Symbas et al. | 128/20 |
| 4,637,377 | 1/1987 | Loop | 128/1 R |
| 4,646,747 | 3/1987 | Lundback | 128/643 |
| 4,718,418 | 1/1988 | L'Esperance, Jr. | 128/303.1 |
| 4,736,749 | 4/1988 | Lundback | 128/643 |
| 4,808,163 | 2/1989 | Laub | 604/105 |
| 4,854,318 | 8/1989 | Solem et al. | 128/346 |
| 4,865,019 | 9/1989 | Phillips | 128/20 |
| 4,962,758 | 10/1990 | Lasner et al. | 128/41 |
| 4,989,587 | 2/1991 | Farley | 128/20 |
| 4,991,578 | 2/1991 | Cohen | 128/419 |
| 5,009,660 | 4/1991 | Clapham | 606/166 |
| 5,011,469 | 4/1991 | Buckberg et al. | 604/4 |
| 5,053,041 | 10/1991 | Ansari et al. | 606/148 |
| 5,108,412 | 4/1992 | Krumeich et al. | 606/166 |
| 5,167,223 | 12/1992 | Koros et al. | 128/20 |
| 5,171,254 | 12/1992 | Sher | 606/166 |
| 5,287,861 | 2/1994 | Wilk | 128/898 |
| 5,365,921 | 11/1994 | Bookwalter et al. | 128/20 |
| 5,372,124 | 12/1994 | Takayama et al. | 128/4 |
| 5,374,277 | 12/1994 | Hassler | 606/207 |
| 5,425,705 | 6/1995 | Evard et al. | 604/28 |
| 5,437,651 | 8/1995 | Todd et al. | 604/313 |
| 5,472,438 | 12/1995 | Schmit et al. | 606/1 |
| 5,509,890 | 4/1996 | Kazama | 600/37 |

(List continued on next page.)

FOREIGN PATENT DOCUMENTS

| | | |
|---|---|---|
| 293760 | 8/1916 | Germany . |
| WO 94/18881 | 9/1994 | WIPO ............... A61B 1/00 |
| WO 95/01757 | 1/1995 | WIPO ............... A61B 19/00 |
| WO 95/15715 | 6/1995 | WIPO ............... A61B 8/12 |
| WO 96/00033 | 1/1996 | WIPO ............... A61B 17/00 |

OTHER PUBLICATIONS

Th. Lavergne et al., "Transcatheter Radiofrequency Ablation of Atrial Tissue Using a Suction Catheter," *PACE*, 12:177–186 (1989).

*Primary Examiner*—Michael Buiz
*Assistant Examiner*—Jonathan Do Goldberg
*Attorney, Agent, or Firm*—Gary Cary Ware & Freidenrich; June M. Learn

[57] ABSTRACT

A device is provided for holding an anastomotic site of a coronary artery motionless and bloodless during surgery is provided. The invention device comprises a suction body with a flexible channel that adheres under suction to the beating heart and surrounds the coronary artery while providing a central opening to expose the anastomotic site for surgery. Suction is built up in the flexible channel by means of an exhaust tube attached thereto. By use of the invention device, an anastomotic site can be held motionless and bloodless during beating heart surgery.

7 Claims, 5 Drawing Sheets

U.S. PATENT DOCUMENTS

| | | | |
|---|---|---|---|
| 5,545,123 | 8/1996 | Ortiz et al. | 600/235 |
| 5,613,937 | 3/1997 | Garrison et al. | 600/201 |
| 5,727,569 | 3/1998 | Benetti et al. | 128/898 |
| 5,782,746 | 7/1998 | Wright | 600/37 |
| 5,799,661 | 9/1998 | Boyd et al. | 128/898 |
| 5,827,216 | 10/1998 | Igo et al. | 604/176 |
| 5,836,311 | 11/1998 | Borst et al. | 606/191 |

DEVICE TO HOLD AN ANASTOMOTIC SITE OF CORONARY ARTERY MOTIONLESS AND BLOODLESS FOR THE BYPASS OPERATION

RELATED APPLICATIONS

This application relies for priority under 35 U.S.C. §119 (e) upon Japanese patent application No. 9-44317, filed Feb. 27, 1997, and International application No. PCT/JP97/04230, filed Nov. 20, 1997, each of which is incorporated herein by reference.

BACKGROUND OF THE INVENTION

1. Technical Field

The present invention relates to the improvement of a device to hold an anastomotic site of coronary artery motionless and bloodless for the bypass operation, more in details, it relates to said device wherein the coronary artery bypass operation can be securely performed on the beating heart with an anastomotic site of the artery motionlessly and bloodlessly held in a safe and stable fashion.

The coronary artery (C) is a blood vessel to supply blood containing oxygen and nutrition to the myocardium of the heart (H) in order to keep the heart in good shape and consists of a right coronary artery (16) and a left coronary artery (7) both originating from the foot of sinus aortae (8). If there happens malfunction in the coronary artery (9) such as stenosis, occlusion and contracture, etc., the blood circulation of the artery is interrupted so that the discrepancy arises between the quantity of oxygen and nutrition actually supplied to the myocardium and that normally required therefore, with the result that ischemic heart diseases such as primary (cardiac arrest, angina pectoris, myocardial infarction, heart failure and arrythmia are invited and those who suffer from those diseases go in peril of their lives.

2. Prior Art

In light of the foregoing, it has been recently recognized that coronary artery bypass surgery is effective to cure those who suffer from such ischemic heart diseases as mentioned above. As a result of it, this surgery has become popular among the cardiovascular surgery practitioners.

In this connection, there are such well-known methods of the coronary artery surgery as a so-called "venous bypass grafting" whereby a circumventive blood vessel is formed by bypassing a venous blood vessel excised from the lower limb between the proximal side of the artery (in the direction of sinus aortae) and the distal side thereof. In addition, there is a so-called "in situ arterial grafting" whereby an appropriate arterial blood vessel such as an internal thoracic artery is led for anastomosis to the distal side of the coronary artery, which has fallen short of oxygen due to deteriorated blood circulation, thereby, supplying arterial blood to the distal side thereof. However, the former grafting method whereby a special circumventive blood vessel is formed between the proximal side and the distal side as mentioned above is not good at grafting patency in the long run because venous valves subsist in the venous blood vessel excised from the lower limb. Under the circumstances, there is a recent tendency for the cardiovascular surgery practitioners to rather use the latter grafting method than the former. In turn, even in the latter grafting method utilizing an arterial blood vessel, there are some cases where a so-called "free arterial grafting" is performed whereby an arterial blood vessel is excised in the same way as the former so as to form a circumventive vessel between the proximal side of the artery (in the direction of sinus aortae) and the distal side thereof. In this case, it is an arterial blood vessel that is used as a grafting material, but it is much inferior to the latter grafting method because the vessel cells become extinct after the vessel has been excised, though it could be better than the former. For this reason, except for insignificant coronary artery related diseases, the latter method is normally adopted for such coronary artery diseases as being likely to risk the patients' lives.

Not to change the subject, even with such latest grafting method as "in situ arterial grafting" as mentioned above, the coronary artery bypass surgery is performed by using a lung-heart machine with the patients' heartbeat halted. This is because it is prerequisite to temporarily halt the heart for accurate dissection and anastomosis in view of the fact that arterial blood is incessantly pressurized to flow into the coronary artery in addition to the fact that said artery has so small diameter of 1 mm to 2.5 mm that careful surgical operation must be performed.

However, it surely brings about big worry for the patient to halt his/her heart even though he/she knows that it temporarily stops. This causes the patient to hesitate accepting the coronary artery bypass surgery. Seldom heard, but there have been reported a few cases where the heart halted for the coronary artery bypass surgery by means of the state-of-the-art lung-heart machine did not recover after the operation so that the surgery must be sometimes very risky. Moreover, it is a well-known fact that this surgery often causes complications to the patients and badly affects them not only during operation, but also after it when they recover themselves from the operation. For your reference, it is a medical practice in Japan that after the patients having been placed under the strict supervision of the medical staff in an intensive care unit for three to seven days after the surgery, they are shifted to a general nursing room where they stay for about one month. Thereafter, they are obliged to stay at home for at least three months till they reinstate themselves at work.

Under the circumstances, the coronary artery bypass surgery by means of minimally invasive thoracotomy undertaken on the beating heart that is professionally called a minimal invasive coronary artery bypass surgery has been proposed in the Western hemisphere since around 1994. The number of the Japanese cardiovascular practitioners who tries to undertake this surgery has gradually increased since then so that the Japanese patients are also now open to this surgery to do without a lung-heart machine. The convenience with such coronary artery surgery as mentioned above where it is undertaken on the patient's beating heart or free from a lung-heart machine is practically shown in the fact reported by a Western academy of medicine advanced in the cardiovascular surgery that an anonymous patient recovered himself from the operation quickly enough to leave hospital for a few days after the operation and reinstate himself at work after one week therefrom. In this regard, since this surgery does not require either a lung-heart machine into which such an expensive integrated circuit of disposable type is incorporated as amounting to about 300,000 yens in Japanese currency unit as of 1997 or an artificial lung amounting to about 200,000 to 300,000 yens in Japanese currency unit as of 1997, it results that the medical expenses are greatly reduced in the patients' favor.

However, for such coronary artery bypass surgery as mentioned above, because the coronary artery having a very small diameter must be dissected and then such an appropriate arterial blood vessel as an internal thoracic artery must be led for anastomosis thereto, it requires an extremely high-advanced surgical skill to quickly, but securely anastomose those two arterial blood vessels on the surface of the heart which continuously beats and which it is very hard to visually observe due to the bleeding. That is to say, according to the recent coronary artery bypass surgery undertaken on the patient's beating heart, the coronary artery is temporarily occluded by performing a looping ligation on both the proximal and distal sides of the artery to be performed anastomosis with such monofilament made of low poisonous synthetic resin such as polypropylene and polyethylene or such venom-free synthetic rubber filament as made of silicone rubber, thereby, anastomosis is performed while the blood flow is suspended. In this case, since it is required to stably fix an arterial portion to be performed anastomosis, the ligature is pulled up so as to fix said portion in suspension. However, In reality, this fixation was hard to succeed not only because it is very likely to cause myocardial tear, injury of the coronary artery branches and such complication as embolism of focal arteriosclerosis in the coronary artery when the circumference of the artery is squeezed with said ligature, but also because a locally suspended portion of the coronary artery is subjected to damage and tear as well as distant coronary stenosis.

In order to solve such inconveniences as encountered with said ligation, a so-called "local myocardial compression device" wherein myocardial portions on both sides of the coronary artery on which anastomosis is performed are compressed with two forked members respectively so as to fix an arterial portion to be anastomosed has been proposed.

It is indeed that the considerably stable fixation of a portion of the coronary artery to be anastomosed can be achieved with this prior device. However, this device is intended to fix a portion to be anastomosed by locally compressing the heart so hard that the considerable deterioration of cardiac function is locally observed particularly in the case of coronary artery bypass surgery undertaken on the patient's beating heart where a lung-heart machine is not supplementarily used for blood circulation, and such issue in the prior arts as bleeding from a locally dissected coronary artery for anastomosis is still pending with the result that such complications on the coronary artery as encountered with said ligation remain unsolved.

DISCLOSURE OF THE INVENTION

In spite of the fact that the coronary artery bypass operation undertaken on the patient's beating heart mostly ends in good result whereby he/she can recover and reinstate himself/herself quickly thereafter, in view of the facts that the cardiovascular surgery practitioners in general could not help hesitating to put the coronary artery bypass operation into practice because it requires an extremely high-advanced skill and a special talent for avoiding the accompanying risks such as complications on the coronary artery, the present invention is to provide a device to securely hold an anastomotic site of the coronary artery motionless for the bypass operation which enables even the practitioners having ordinary surgical skills in the arts to be relieved to undertake said operation on the patient's beating heart.

The present invention is further to provide a device to hold an anastomotic site of the coronary artery motionless for the bypass operation which rarely invites the deterioration of cardiac function during the operation because it does not compress the heart at all.

The present invention is further to provide a practical device to hold an anastomotic site of the coronary artery motionless and bloodless for the bypass operation which can restrain the bleeding from a dissected portion of the coronary artery for anastomosis to the extent that it hardly interrupts the progress of the operation.

The present invention is further to provide a device particularly useful for cardiovascular surgery which is convenient for the surgery operators in charge of the operation to use and does not become a heavy burden on their assistants either and which is so easy to handle that there is no possibility for them to commit operational errors.

The other issues to be solved as well as the conveniences of the present invention are clarified with the following description.

The present invention is characterized in that it has solved the aforesaid technical issues of the prior arts by adopting a device to hold an anastomotic site of the coronary artery motionless and bloodless for the bypass surgery comprising a suction body or a suction means of the heart surface provided with a flexible channel to surround the coronary artery and in the central portion of which a circular opening to expose an arterial portion to be anastomosed is formed and a piping means provided with an exhaust tube to negatively pressurize said flexible channel by drawing off the air therefrom.

To give further comments on the aforesaid means of the present invention to solve the issues of the prior arts, the reason why said suction body (for suction of the heart surface) is adopted in the present invention is because just by pulling up a bit with a holding means such as a handle said suction body and the heart surface clung to each other by abutting the former on the latter in such a manner that the former interposes an anastomotic site of the coronary artery between the proximal side and the distal side of the artery and then drawing off the air from said flexible channel said anastomotic site can be stably held in check without need to forcedly compress the heart as in the case of a conventional local myocardial compression device in the prior arts. Then, the reason why said piping means provided with an exhaust tube to negatively pressurize the flexible channel is adopted in the present invention is because the air can Le drawn off the channel by taking advantage of an exhaust pump to be necessarily equipped in any operation room of whatever hospitals.

DETAILED DESCRIPTION OF THE PREFERRED EMBODIMENT

Hereinafter, the concrete contents of the present invention is in more detail described on the basis of embodiments shown in the accompanying drawings.

(FIRST EMBODIMENT)

Figure 1:
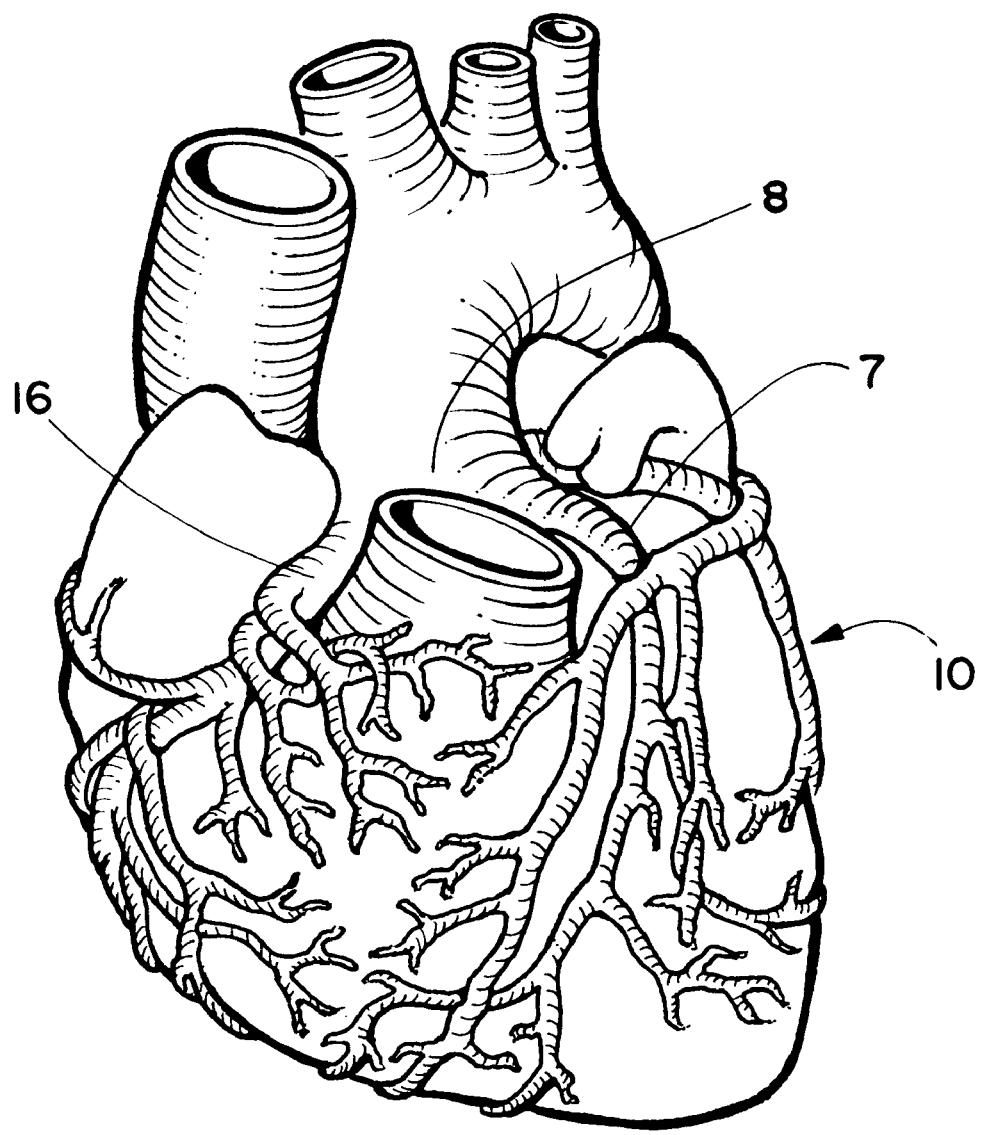
FIG. 1 is a perspective view showing the surroundings of the heart as well as the coronary artery.
Figure 2:
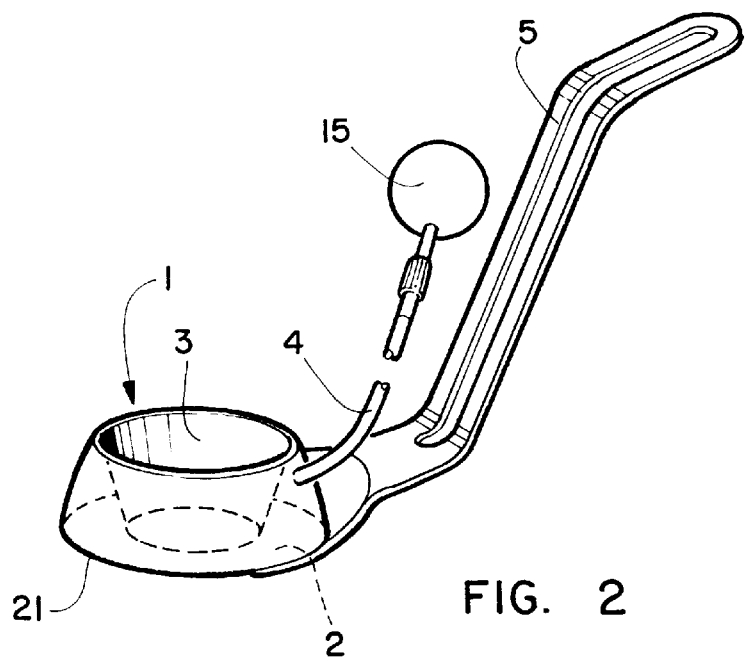
FIG. 2 is a perspective view showing a device described in the first embodiment of the present invention.

The first embodiment of the present invention is as shown in FIG. 2. Numeral (1) indicates a suction body made of silicone rubber and the central portion thereof, surrounded by a flexible channel (2) which is formed in doughnut shape (ring-shaped) and the lower surface of which is open to the air, forms a circular opening (3) to expose an anastomotic site of the coronary artery (9). This opening (3) has sufficient space to expose said site and has about 15 mm in diameter at a smaller section in the present embodiment.

Numeral (4) indicates an exhaust tube made of silicone rubber and engaged to said flexible channel (2) at one end and the other end of which can be connected to an exhaust pump (15).

Numeral (5) indicates a handle made of hard silicone rubber and fixed on the outer surface of said suction body (1). During operation, by means of this handle (5), said suction body (1) is positioned at an anastomotic site of the coronary artery (9) while the device is pulled up a bit with this handle (5) when said suction body (1) and anastomotic site have clung to each other.

The coronary artery (C) bypass surgery procedures by means of the device of the present embodiment (hereinafter, referred as the present device) are as follows.

To begin with, the present device is positioned at an anastomotic site of the coronary artery (9) with a handle (5) in such a manner that said site can be viewed through the opening (3) surrounded by said flexible channel (2). At this time, both the proximal side and the distal side of the coronary artery (9) with regard to said anastomotic site are trod on with suction fringes (21) of said channel (2).

Then, when the air is drawn off the channel (2) by driving said exhaust pump (15), said suction body (1) clings to the surface of the beating heart (10) while the suction fringes (21) of said channel (2) squeeze and occlude both the proximal side and the distal side of the artery (9) so as to stop the blood flow in the artery at both ends. Then, when the suction body (1) has been securely clung to an aimed anastomotic site of the artery (9) and the blood flow has been hampered in the artery (9), the device is pulled up a bit with the handle (5). In this way, the hemostasis of the anastomotic site is completed without need to compress the beating heart (10) at all as well as said site is stably held.

Figure 3:
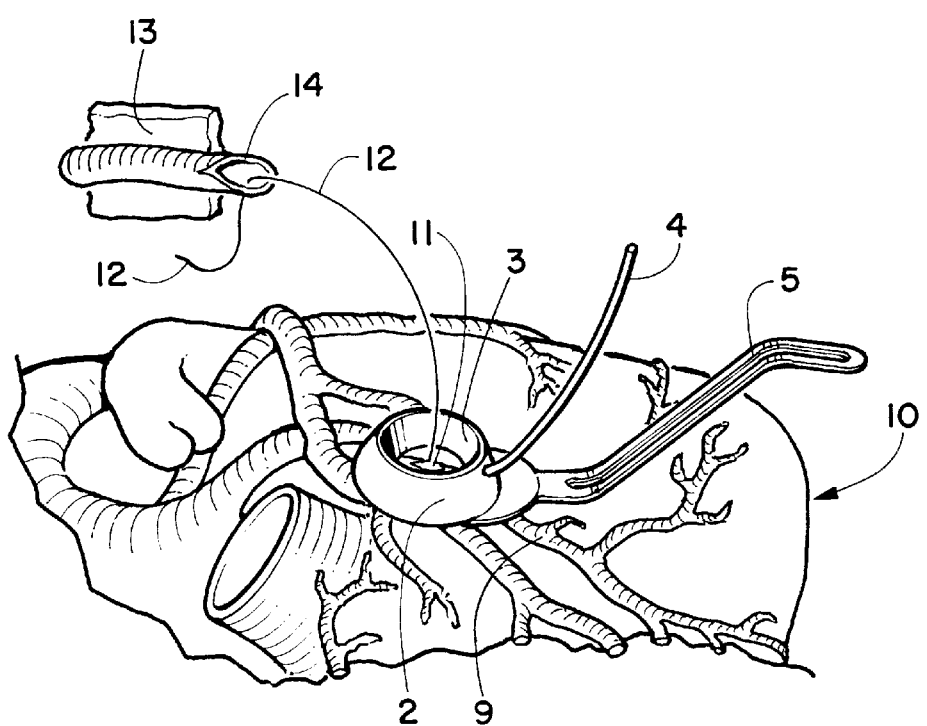
FIG. 3 is a perspective view showing how to use the device of the first embodiment.

Next, an aperture (11) is dissected with a scalpel on the coronary artery (9) exposing through the opening (3) while an internal thoracic artery (or a gastroepiploic artery) (14) is led to said aperture so as to be anastomosed to the coronary artery (9) with a suture (12) as shown in FIG. 3. It should be noted that what is indicated with (13) in FIG. 3 is adipose tissue and musculation stripped off together with said thoracic artery (14) and the artery (I) itself is occluded at a portion not shown in FIG. 3 so as to hamper the blood flow in the artery.

When the thoracic artery (14) has been anastomosed to the aperture (11) of the coronary artery (C), by returning the internal pressure of the flexible channel to the atmospheric pressure, said suction body (1) is detached from the surface of the heart (10) as well as the coronary artery (9) so that the blood flow of the artery (9) resumes as well as the blood supplied from the internal thoracic artery (I) supplementarily flows through the distal side of the artery (9). Thereat, said suction body (1) surrounding the thoracic artery (I) is torn off so as to be removed for disposal. And the surgery ends with the final step to suture the chest. The coronary artery bypass surgery by means of the present device only takes about 90 to 180 minutes in average from the thoracotomy through the suture of the chest so that the fatigue of the patients as well as the burdens on the surgery operators and their assistants such as nurses can be greatly abated.

(SECOND EMBODIMENT)

Figure 4:
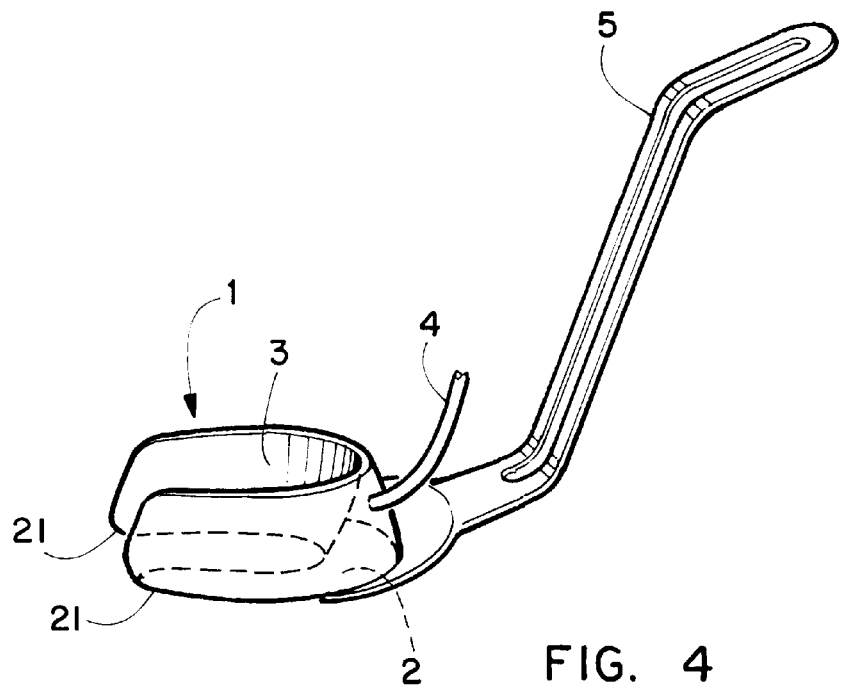
FIG. 4 is a perspective view showing a device described in the second embodiment of the present invention.
Figure 5:
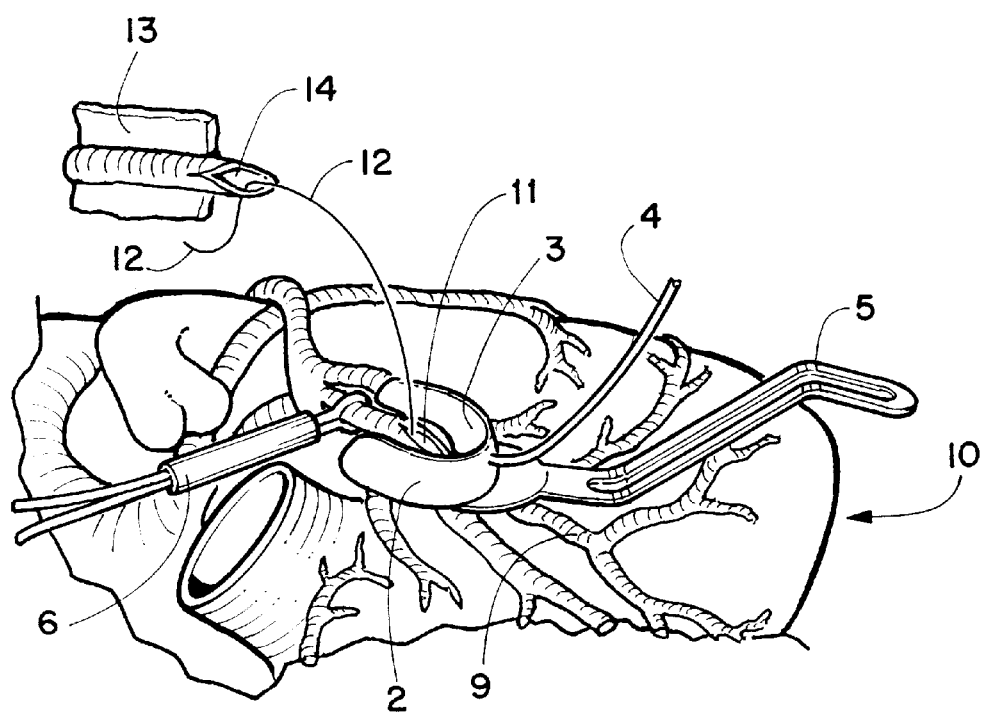
FIG. 5 is a perspective view showing how to use the device of the second embodiment.

The second embodiment of the present invention is as shown in FIG. 4. The sole difference between the present embodiment and the first one is in that the flexible channel (2) of the suction body (1) is formed in horseshoe shape. Accordingly, when the present device has been positioned on the heart surface and an anastomotic site of the coronary artery (9) with a handle (5) so that said site can be viewed through an opening (3) surrounded by the channel (2) and then the air has been drawn off the channel (2) by means of an exhaust pump (P), the blood flow on the distal side of the coronary artery (9) with regard to said anastomotic site is hampered because suction fringes of the channel (2) tread on said distal side so as to occlude it while the blood flow on the proximal side of the artery (9) with regard to said anastomotic site is unaffected because the channel (2) is open to the side of the sinus aortae. Therefore, with the present device, it becomes necessary to take a further step to hamper the blood flow by clamping the proximal side of the coronary artery (9) with a hemostatic tool (6).

The advantage of the present device lies in that the surgery is partly simplified because it can be done without tearing off the suction body (1) after the completion of anastomosis as mentioned in the first embodiment.

(THIRD EMBODIMENT)

Figure 6:
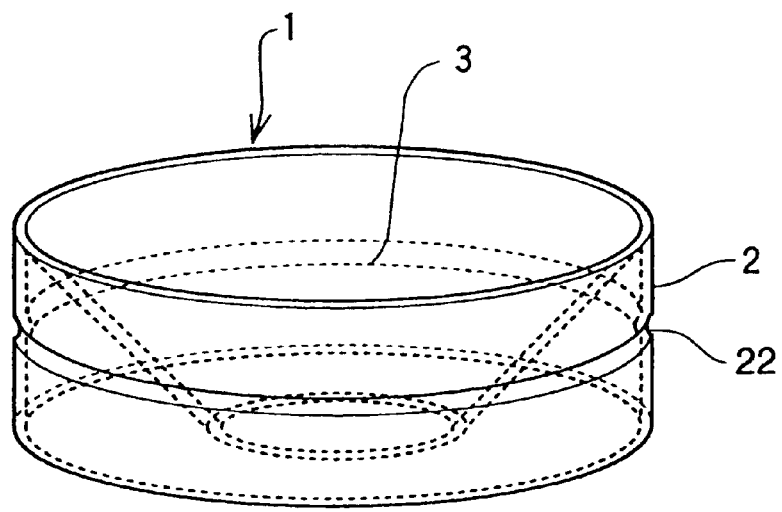
FIG. 6 is a perspective view showing a device described in the third embodiment.
Figure 7:
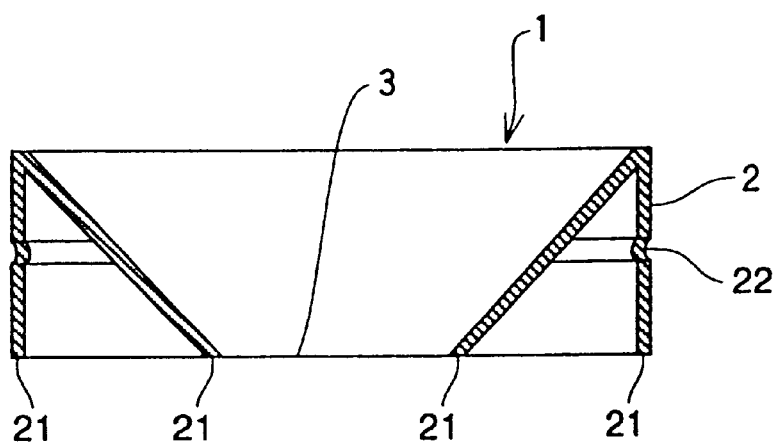
FIG. 7 is an elevational view in section of the device of the third embodiment to show its structure.
Figure 8:
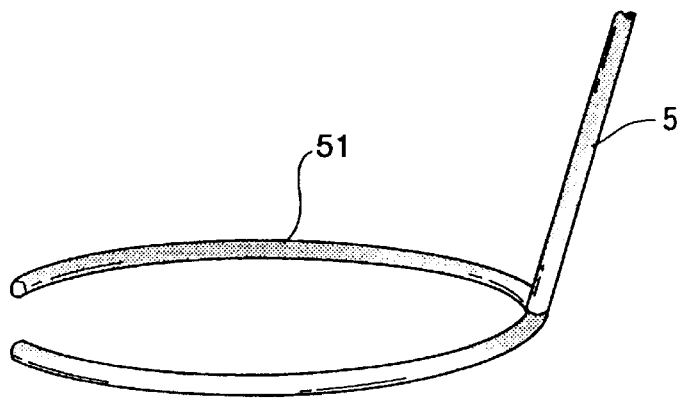
FIG. 8 is an enlarged perspective view of a handle removably mounted on the device of the third embodiment.

The third embodiment of the present invention is as shown in FIG. 6 to FIG. 8. A suction body (1) of the present device is formed in uprightly cylindrical shape while in the central portion thereof surrounded by a flexible channel (2) an opening (3) gradually decreasing in diameter towards the bottom is formed. A concave groove (22) is formed on the outer surface of said flexible channel (2) into which a loop (51) of a handle (5) as shown in FIG. 8 is removably fitted.

The outer surface of the channel (2) of the present device has 3 mm in thickness and the concave groove (22) having 4 mm in depth and 2 mm in width is circumferentially formed in the middle region of said outer surface so as to receive said loop (51) having 2 mm in diameter therein. As a material of the suction body (1), a synthetic rubber such as thermoplastic elastmer fluorine is used in the present embodiment.

(FOURTH EMBODIMENT)

Figure 9:
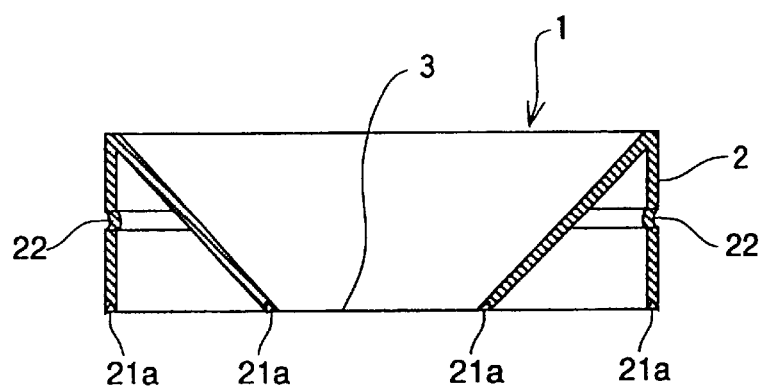
FIG. 9 is an elevational view in section of the device of the fourth embodiment to show its structure.
Figure 10:
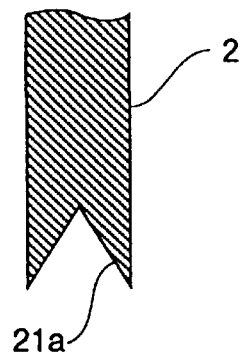
FIG. 10 is a partly exploded end view of a flexible channel of the fourth embodiment to show the shape of a suction fringe thereof.

The fourth embodiment of the present invention is as shown in FIGS. 9 and 10. The basic structure of this embodiment is the same as that of the third one, and the sole difference between the former and the latter is in that reversely wedge-shaped edges (21a) are formed on the suction fringes. When the air has been drawn off the channel (2), the present device more firmly clamps both the proximal side and the distal side of the coronary artery (9) with those reversely wedge-shaped edges (21a) provided on the suction fringes so as to occlude the blood flow of the artery at both ends, with the result that the bleeding from the aperture (11) dissected for anastomosis can be more securely restrained.

EXAMPLES

The present inventor performed the coronary artery bypass surgery on the patients' beating hearts by means of the device described in the first embodiment of the present invention after having experimented it with four canine each weighing 12 kg in average and one pig weighing 50 kg.

(EXPERIMENT)

After the canine and the pig having been performed general anesthesia, an intercostal on the left side of the chest is transversely dissected about 8 cm in length and an interior thoracic artery is peeled off over 5 cm in length. Then, after the heart has been exposed by longitudinally dissecting a pericardium, the device of the first embodiment of the present invention is positioned on an anastomotic site of the coronary artery and then fixedly clung to the heart surface encompassing said anastomotic site by driving an exhaust pump so as to draw off the air from the flexible channel. Thereafter, when the device is pulled up a bit with the handle, an incomparably stable operation field can be obtained even though the heart is beating. Then, an aperture is formed on the coronary artery (i.e., a left anterior descending artery) by dissecting said artery by 3 to 4 mm in length and then anastomosed to said thoracic artery led thereto by means of continuous suture. In this experiment, although no ligature is used to occlude the blood flow of the distal side of the coronary artery, there is observed no bleeding from the aperture. In spite of the fact that tachycardia is observed during the experiment, anastomosis can be easily performed on the beating heart and the anastomotic site of the coronary artery sutured with the thoracic artery remains stably intact. Then, when the exhaust pump has been turned off in order to tear off and remove the device after the completion of anastomosis, it is confirmed that the blood flow of the thoracic artery of four canine respectively is measured at 24±3.41 ml/min showing a favorable result and no damage is observed on the heart surface of each canine to which the device has been fixedly clung.

(CLINICAL TEST)

In the first place, the coronary artery bypass surgery which uses a conventional lung-heart machine together with the device embodied in the present invention has been performed on three cases. In each case, the device has been fixedly clung to the heart surface surrounding an anastomotic site of the left anterior descending artery by exhausting the air from the flexible channel. Thereafter, when the device is pulled up a bit with the handle in the same way as the aforesaid experiment, an incomparably stable operation field can be obtained even though the heart is beating.

Then, an epicardium tissue in front of the anastomotic site of the left anterior descending artery has been longitudinally peeled off by 8 mms with a scalpel. Even in this case, said tissue could be safely peeled off by virtue of an incomparably stable operation field obtained with the device of the present invention.

After having performed the supplemental blood circulation by means of said lung-heart machine while having occluded the blood flow from the aortae and administered a myocardial protecting liquid so as to halt the heart, the device was removed from the heart surface for a while in order to confirm its hemostatic effect and then an aperture was formed on the left anterior descending artery by dissecting said artery by 4 mms in length. As a result of it, the bleeding from both the proximal and distal sides of the anastomotic site was observed. Thereat, once the device was fixedly clung to the heart surface surrounding said aperture again by exhausting the air from the flexible channel, said bleeding has come to be barely observed.

On the other hand, the aforementioned minimal invasive coronary artery bypass surgery which has been developed in the Western countries was undertaken on the beating heart of six cases respectively without using said lung-heart machine at all.

After each case has been performed general anesthesia before the operation, the fifth left intercostal was transversely dissected about 8 cm and the interior thoracic artery was peeled off by 7 cm. Then, the heart was exposed by longitudinally dissecting the pericardium.

Thereafter, the device of the present invention was positioned on an anastomotic site of the left anterior descending artery as well as the heart surface surrounding said site and then fixedly clung thereto by driving the exhaust pump. Then, when the device was held by pulling it up a bit with the handle, the surgery operator could obtain an incomparably stable operation field even though the heart was beating.

Thereafter, an aperture was opened on the left anterior descending artery by dissecting said artery to which the interior thoracic artery preliminarily led to the aperture was anastomosed by means of continuous suture. Under this minimal invasive coronary artery bypass surgery, since the use of the device embodied in the present invention enabled the anastomotic site to be very stably fixed and the bleeding from said site to be effectively restrained, the surgery could be very quickly and easily performed, but with accuracy. In this surgery, although no ligature was used at all on the distal side of the coronary artery for occlusion of the blood flow, no bleeding from the aperture was observed. In addition, all the cases (i.e., 6 patients) that have undergone this surgery without using a lung-heart machine awoke immediately after the operation and some of them were allowed to leave the intensive care room only one day after they had been placed there while the others were allowed to leave two days at longest so that it took rather shorter time for the patients to restore themselves in comparison with the conventional bypass surgery using a lung-heart machine. Moreover, it was confirmed after the operation by means of coronary angiography that the grafting patency was pretty good and no abnormity such as stenosis was observed at all in said site. Further additionally, only a small quantity of heparin sodium was required to be administered because the lung-heart machine is not used and the bleeding from the anastomotic site was hardly observed. The six cases subject to the clinical test are each outlined as follows. The first case is a 79 year-old man who has been suffering from the complications of cerebral infarction and been troubled with the symptom of low pulmonary function before the operation. The outcome of the operation was good enough for him to leave the hospital 10 days thereafter. The second case is a 59 year-old man who has been suffering from ischemic cardiomyopathy and the complications of diabetes. The outcome of the surgery was good enough for him to leave the hospital two weeks thereafter. The third case is a 66 year-old man who have been suffering from the complications of cerebral infarction before the operation. The outcome of the operation was good enough for him to leave the hospital two weeks thereafter. The fourth case was a 60 year-old woman who left the hospital in good shape 8 days after the operation. The fifth case is a 56 year-old man who left the hospital in good shape 9 days after the operation. And the sixth and last case is a 60 year-old man who left the hospital in good shape 9 days after the operation. In the conventional coronary artery bypass operation, it took about one month after the operation to perform angiographic examination on the anastomotic site of the artery while it took only one week to do so in the present case. This is because the patients could recover from the operation far more quickly than In the conventional bypass surgery in view of the fact that the present case requires the heart neither to be halted nor to be forcedly compressed by external force.

The embodiments and examples of the present invention have been substantially disclosed up to here. It should be understood that the present invention is not limited to those embodiments and examples, but it can be modified in various manners within the scope of the accompanying patent claims. For instance, as a material of the suction body (1) of the present device, such synthetic resin having rubber elasticity as soft vinyl chloride and soft polyethylene can be also adopted. The shape of both the suction body (1) and the opening (3) of the present device is not limited to the circular one, but it can be also formed in an oval or square shape. Moreover, the suction surface of the present device can be also formed in a concave shape in accordance with the outline of the heart surface.

Furthermore, the handle (5) of the present device is an additional structural element at the applicant's disposal so that the suction body (1) itself can be structured in such a manner that it can be easily held by hand or a holding means can be given to the exhaust tube (4). Those modified embodiments also belong to the technical scope of the present invention.

As having been described up to here with the aforesaid embodiments and examples, according to the device of the present invention, an anastomotic site of the coronary artery and the heart surface surrounding said site are held in slight suspension by taking advantage of suction pressure of the suction body. Therefore, the arterial blood vessel to be anastomosed is fixed in a stable manner even though the heart is beating so that it becomes much easier to dissect said arterial blood vessel and perform anastomosis by means of suture. Furthermore, the heart surface is not compressed by external force so that there is hardly any possibility to cause such deterioration of cardiac function during the operation as in the case of the prior arts. Because of those favorable surgical conditions, it makes it possible to securely perform the coronary artery bypass operation without a hitch.

Since the suction fringes of the flexible channel of the present device tread on the coronary artery in such a manner that they hold the heart in slight suspension without compressing it excessively so as to occlude said artery, the bleeding from an aperture formed on the artery for anastomosis can be restrained to the extent that it hardly affects the progress of the operation with the result that the present device provides an adequate operation environment to the cardiovascular surgery practitioners.

Moreover, as mentioned above, the present device is so easy to handle that it is little burden on either the (cardiovascular surgery operators nor their assistants who perform the coronary artery bypass operation which requires very demanding jobs, while there is no possibility for them to commit operational errors during the operation. Conventionally, the coronary artery bypass operation performed on the beating heart was handled only by the cardiovascular surgery practitioners who have acquired a special surgical skill. However, the device of the present invention also enables other practitioners having ordinary skills in the arts to perform said bypass operation. Therefore, in view of the safety and convenience to use, the present device is far incomparable to the conventionally well-known local myocardial compression device.

In this way, the present device can not only abate burden on both the patients and the cardiovascular surgery practitioners concerning the coronary artery bypass operation, but also solve the prior issue where said operation was handled only by the practitioners having a special surgical skill. Therefore, it is worth mentioning that the present device greatly contributes to the further improvement of the cardiovascular surgery.

What is claimed is:

1. A device for holding an anastomotic site of a coronary artery motionless and bloodless for bypass surgery, said device comprising a suction body provided with a flexible channel to surround the coronary artery and to cling to the heart surface, wherein said flexible channel is open to the air on one side and said suction body is provided with an opening in the central portion to expose the anastomotic site of said coronary artery for surgical operation and an exhaust tube is engaged to said flexible channel to draw off the air therefrom.

2. A device according to claim 1, wherein said flexible channel is formed in doughnut shape.

3. A device according to claim 1, wherein said flexible channel is formed in horseshoe shape.

4. A device according to claim 1, wherein a handle is provided on the outer surface of said suction body.

5. A device according to claim 4, wherein said handle is removably mounted on the outer surface of said suction body.

6. A device according to claim 1, wherein said flexible channel is made of non-toxic synthetic resin having rubber elasticity.

7. A device according to claim 1, wherein reversely wedge-shaped edges are formed on suction fringes of the flexible channel.

* * * * *